(12) United States Patent
Petrov et al.

(10) Patent No.: US 7,170,068 B2
(45) Date of Patent: Jan. 30, 2007

(54) METHOD AND SYSTEM FOR DISCHARGING A SAMPLE

(75) Inventors: Igor Petrov, Holon (IL); Oren Zoran, Ramat-Gan (IL); Juergen Frosien, Riemerling (DE)

(73) Assignee: Applied Materials, Israel, Ltd., Rehovot (IL)

( * ) Notice: Subject to any disclaimer, the term of this patent is extended or adjusted under 35 U.S.C. 154(b) by 82 days.

(21) Appl. No.: 11/129,463

(22) Filed: May 12, 2005

(65) Prior Publication Data
US 2006/0255288 A1    Nov. 16, 2006

(51) Int. Cl.
*G01K 1/08* (2006.01)
*H01J 3/14* (2006.01)
*H01J 3/26* (2006.01)
*G01N 23/00* (2006.01)
*G21K 7/00* (2006.01)

(52) U.S. Cl. .................. 250/398; 250/310; 250/311; 250/307

(58) Field of Classification Search ............ 250/398, 250/310, 311, 307
See application file for complete search history.

(56) References Cited

U.S. PATENT DOCUMENTS

| | | | | |
|---|---|---|---|---|
| 5,885,354 | A | * | 3/1999 | Frosien et al. ......... 118/723 FE |
| 6,182,605 | B1 | * | 2/2001 | Frosien .................. 118/723 EB |
| 6,555,815 | B2 | * | 4/2003 | Feuerbaum et al. ........ 250/310 |
| 2004/0169140 | A1 | * | 9/2004 | Schlichting ................. 250/310 |

* cited by examiner

*Primary Examiner*—Jack Berman
*Assistant Examiner*—Jennifer Yantorno
(74) *Attorney, Agent, or Firm*—Tarek N. Fahmi (57) ABSTRACT

A method for discharging a sample, the method includes: determining whether to discharge a negatively charged area of a sample or to discharge a positively charged area of the sample; and injecting gas, via an electrode and gas supply component, or setting a first electrode to a first voltage and set the electrode and gas supply component to a second voltage, in response to the determination. A system including: a first electrode adapted to be set to at least a first potential; an electrode and gas supply component, adapted to be set to at least a second potential and to selectively supply gas to a vicinity of the sample; wherein at least one out of the first electrode and the electrode and gas supply component are positioned close to the sample.

19 Claims, 10 Drawing Sheets

METHOD AND SYSTEM FOR DISCHARGING A SAMPLE

FIELD OF THE INVENTION

The invention relates to a method and system for discharging a sample such as but not limited to a wafer or reticle that is scanned by a charged particle beam.

BACKGROUND OF THE INVENTION

Charged particle beam columns are typically employed in scanning electron microscopy (SEM), which is a known technique widely used in the manufacture of semiconductor wafers, being utilized in a CD metrology tool, the so-called CD-SEM (critical dimension scanning electron microscope), and a defect review SEM (DF-SEM). In SEM, the region of a sample to be examined is two-dimensionally scanned by means of a focused primary beam of electrically charged particles, usually electrons. Irradiation of the sample with the primary electron beam releases secondary (and/or backscattered) electrons. The secondary electrons are released at that side of the sample at which the primary electron beam is incident, and move back to be captured by a detector, which generates an output electric signal proportional to the so-detected electric current. The energy and/or the energy distribution of the secondary electrons is indicative of the nature and composition of the sample.

Various prior art CD-SEMs and method for measuring critical dimensions are illustrated in the following U.S. patent applications which are incorporated herein by reference: U.S. patent application publication number 20030015699 of Su, titled "Integrated critical dimension control for semiconductor device manufacturing"; U.S. patent application publication number 20050048654 of Wu, titled "Method of evaluating reticle pattern overlay registration"; U.S. patent application publication number 20040173746 of Petrov, et al., titled "Method and system for use in the monitoring of samples with a charged particles beam"; U.S. patent application publication number 20040056207 of Petrov, et al., titled "Deflection method and system for use in a charged particle beam column"; U.S. patent application publication number 20030218133 of Petrov, et al., titled "Charged particle beam column and method for directing a charged particle beam", and U.S. patent application publication number 20030209667 of Petrov, et al., titled "Charged particle beam apparatus and method for inspecting samples.

SEM includes such main constructional parts as an electron beam source (formed with a small tip called "electron gun"), an electron beam column, and a detector unit. The detector unit may be located outside the path of the primary beam propagation through the column, or may be located in the path of the primary beam (the so-called "in-column" or "in-lens" detector). The electron beam column includes, inter alia, a beam focusing/deflecting arrangement formed by a lens assembly and a deflector assembly. The deflection of the primary beam provides for scanning the beam within a scan area on the sample, and also for adjusting incidence of the primary beam onto the sample (an angle of incidence and/or beam shift), as well as directing the secondary beam to the detector.

In SEM, in order to reduce the "spot" size of the electron beam (up to nanometers) and thus increase the image resolution, a highly accelerated electron beam is typically produced using accelerating voltages of several tens of kilovolts and more. Specifically, the electron optic elements are more effective (i.e. produce smaller aberrations) when the electrons are accelerated to high kinetic energy. However, in order to avoid damaging a sample (resist structure and integrated circuit) that might be caused by such a highly energized electron beam, the electron beam is decelerated just prior to impinging onto the sample. Deceleration of the electrons can generally be accomplished by selectively creating a potential difference between the pole piece of a magnetic objective lens and the sample. Alternatively, the same effect can be achieved by actually introducing electrodes having selective potential applied thereto.

Some systems of the kind specified utilize the lens assembly in the form of a combination of a magnetic objective lens and an electrostatic lens, the so-called "compound magnetic-electrostatic lens" (e.g., EP 1238405 and EP 1045425, both assigned to the assignee of the present application). The electrostatic part of the compound magnetic-electrostatic lens is an electrostatic retarding lens (with respect to the primary charged particle beam), and has electrodes held at different potentials, one of the two electrodes being formed by an anode (which is typically in the form of a tube defining a primary beam drift space for the primary beam propagation to the sample, such as anode 11 of FIGS. 2–7) arranged within a magnetic objective lens along its optical axis, and the other electrode being a metallic cap provided below the magnetic objective lens. The sample actually presents the third electrode of the electrostatic lens. The electric field created by the electrostatic lens in the vicinity of the sample appropriately decelerates the primary beam and also facilitates the extraction of secondary charged particles from the sample.

U.S. Pat. No. 5,780,859 of Feuerbaym et al., which is incorporated herein by reference, describes a prior art electrostatic-magnetic lens arrangement.

Another known problem of the inspection systems of the kind specified is associated with locating defects (foreign particles) on patterned surfaces. The pattern is typically in the form of a plurality of spaced-apart grooves. To detect the existence of a foreign particle located inside a narrow groove, it is desirable to tilt the scanning beam with respect to the surface, which tilting should be applied to selective locations on the specimen. A tilt mechanism may be achieved by mechanically tilting the sample holder relative to the charged particle beam column, and/or by electronically tilting the primary beam propagation axis. The electronic tilt is implemented by the deflector assembly, which may include one or more deflectors. This may for example be a magnetic deflector integrated into a magnetic objective lens (WO 01/56056), which has an excitation coil and upper and lower pole pieces.

US 20040056207, assigned to the assignee of the present application discloses a deflection system including a magnetic deflector (core and pole pieces electrically connected to the core) and a pole piece assembly, which has a portion made of a soft magnetic material and is formed with an opening for a charged particle beam passage therethrough. The pole piece assembly is accommodated so as to be at least partly located within the magnetic field of the magnetic deflector to thereby conduct at least a portion of the magnetic field created by the deflector through the pole piece assembly towards the opening. This arrangement increases the effectiveness of deflection and facilitates operation with the tilt mode, by increasing a magnetic field for a given electric current through the excitation coils of the deflector. This allows for obtaining a desirably high deflecting magnetic field within the closest vicinity of the sample at the optical axis of the lens arrangement, without increasing a working distance, also in cases where the compound magnetic-electrostatic lens is used.

Generally, the image resolution of a charged particle beam column can be improved by increasing the anode voltage. However, this might result in a breakdown in the system operation. On the other hand, an increase of a negative voltage (in absolute value) applied to a sample under inspection when operating with a charged particle beam column in which the pole pieces of a magnetic deflector are grounded, which is typically the case, is also limited by the breakdown condition at a given working distance. The term "working distance" is typically referred to as a distance between the electrode of the lens arrangement closest to the sample's plane (cap-electrode in the present case) and the sample's plane. This distance should be as small as possible, and the minimal possible working distance is typically defined by an arcing problem.

Preciseness of measurements, such as CD measurements on semiconductor wafers and especially on lithographic masks (reticles), typically suffers from an effect of negative charging of the sample's surface by a scanning beam of charged particles, which causes an image drift. The gas supply into the vicinity of the sample and ionization by the scanning beam allow for reducing negative charging of the sample's surface due to the precipitation of positive ions onto the sample's surface, and thus allow for increasing the precision of CD measurements.

The gas supply unit typically used in a DR-SEM includes a special nozzle tube for feeding the gas. The nozzle is mounted on the side surface of a conical objective lens such that the outlet opening of the nozzle is located proximate of the beam opening of the objective lens. This configuration is, however, unsuitable for a CD-SEM that typically utilizes a substantially flat cap-electrode and requires a smaller working distance (about 0.8 mm, instead of 1.5 mm used in DR-SEM). The conventional configuration of a gas supply unit used in the CD-SEM suffers from that disabling the cap electrode breaks the tightness connection between the electrode and the gas supply unit, because a gas tube thereof is connected to a holder separate from the cap electrode. Moreover, the connection zone is too small and therefore cannot be sufficiently reliable. Also, this configuration does not allow for using the so-called post-tilt deflector aimed at providing an on-axis tilt of a primary beam.

An example of the conventional gas supply system is described in U.S. Pat. No. 6,182,605. An apparatus for particle beam induced modification of a specimen includes a source for generating a particle beam, nozzles for supplying a gas in the region of the specimen, and electrodes which can be supplied with a variable voltage. These electrodes are forming a tube and the nozzles, being integrated in the electrodes, are leading into the tube.

U.S. Pat. No. 6,555,815, assigned to the assignee of the present application, discloses a charged particle beam column, where charging of the specimen is avoided or reduced by injecting inert gas onto the sample's surface. In order to avoid interactions with the electron optics, various embodiments are disclosed for providing a rotationally symmetrical nozzles and/or electrodes. Additionally, embodiments are disclosed wherein a plurality of gas conduits are arranged in a rotationally symmetrical manner. Alternatively, the conduit is incorporated into an element of the electron optics, such as the magnetic lens. Also, in order to reduce or eliminate interaction of the electrons with the gas molecules, embodiments are disclosed wherein the gas is pulsated, rather than continually injected.

Gas supply does not prevent positive charging. Positive charging can be reduced by introducing a negative potential above the charged sample. This negative potential induced secondary electrons to return to the object.

SUMMARY OF THE INVENTION

A method for discharging a sample, the method includes: determining whether to discharge a negatively charged area of a sample or to discharge a positively charged area of the sample; and injecting gas, via an electrode and gas supply component, or setting a first electrode to a first voltage and set the electrode and gas supply component to a second voltage, in response to the determination.

A system including: a first electrode adapted to be set to at least a first potential; an electrode and gas supply component, adapted to be set to at least a second potential and to selectively supply gas to a vicinity of the sample; wherein at least one out of the first electrode and the electrode and gas supply component are positioned close to the sample.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE INVENTION

Figure 1:
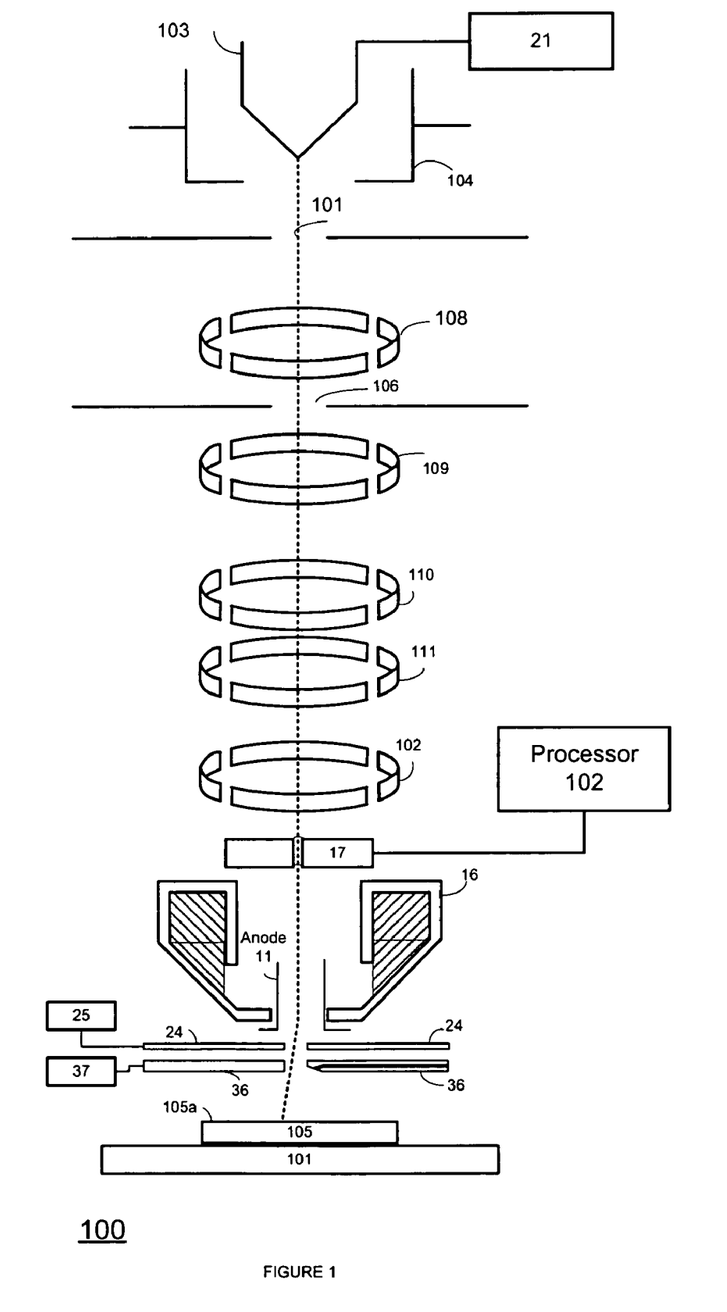
FIG. 1 schematically illustrates a system according to an embodiment of the invention.

The following figures refer to certain CD-SEM. It is noted that this configuration, and especially that described in FIG. 1 are provided as a non-limiting example. The invention can be applied in other SEMs and in CD-SEMs that have different configurations. It can also be applied to charged particle beams that differ from electron beams. This may include ion beams.

FIG. 1 illustrates a system such as CD-SEM 100 according to an embodiment of the invention. CD-SEM 100 includes an electron gun 103 emitting an electron beam 101, which is extracted by the anode 104. The objective lens 16 focuses the electron beam on the specimen surface 105a. The beam is scanned over the specimen using the scanning deflection unit 102. An alignment of the beam to the aperture 106 or a desired optical axis respectively can be achieved by the deflection units 108 to 111. As a deflection unit coils, electrostatic modules in the form of charged plates or a combination of coils and electrostatic deflectors can be used. Conveniently, at least one deflection coil is positioned between the objective lens and the sample.

It is noted that according to other embodiments of the invention a scan deflector is located between the in-lens detector 17 and the sample.

In-lens detector 17 is able to detect secondary electrons that escape from the specimen 105 at a variety of angles with relatively low energy (3 to 50 eV). Measurements of scattered or secondary electrons from a specimen can be conducted with detectors in the form of scintillators connected to photomultiplier tubes or the like. Since the way of measuring the signals does not influence the inventive idea in general, this is not to be understood as limiting the invention. It is noted that the CD-SEM may include, additionally or alternatively, at least one out-of lens detector.

Detection signals are processed by a processing unit 102 that may have image processing capabilities and is able to process the detection signals in various manners. A typical processing scheme includes generating a waveform that reflects the amplitude of the detection signal versus the scan direction. The waveform is further processed to determine locations of at least one edge, and other cross sectional features of inspected structural elements.

The different parts of the system are connected to corresponding supply units (such as high voltage supply unit 21) that are controlled by various control units, most of them are omitted from the figure for simplifying the explanation. The control units may determine the current supplied to a certain part, as well as the voltage.

CD-SEM 100 includes a double deflection system that includes deflection units 110 and 111. Thus, the beam tilt introduced in the first deflection unit 110, can be corrected for in the second deflection unit 111. Due to this double deflection system, the electron beam can be shifted in one direction without introducing a beam tilt of the electron beam with respect to the optical axis.

As mentioned above, the tilt can, additionally or alternatively, performed below (downstream direction) of the objective lens.

CD-SEM 100 also includes first electrode 24 that can receive voltage from supply unit 25 and also includes a electrode and gas supply component 36 that can receive voltage from supply voltage 37 and receive gas from gas supply system (not shown).

The objective lens 16 can include a combination of a magnetic lens and an electrostatic lens. The magnetic lens usually includes at least two pole pieces defining a magnetic lens gap therebetween. The electrostatic lens is usually formed by one or more electrodes that can even include the sample itself. At least one electrode serves for regulating an electric field created within the vicinity of the sample.

FIGS. 2–7 illustrates various electrode arrangements 12–16 according to various embodiments of the invention.

In general, the first electrode 24 can be located above the electrode and gas supply component 36 or can be located below the electrode and gas supply component 36.

If the first electrode 24 is located above the electrode and gas supply component 36 and if the system performs discharging of a negative charge the then first electrode 24 can be provided with a positive voltage that can range between zero and few hundred volts. The electrode and gas supply component 36 can be provided by a positive voltage that is lower than the positive voltage provided to the first electrode 24.

If the first electrode 24 is located below the electrode and gas supply component 36 and if the system performs discharging of a negative charge then the voltage supplied to the first electrode 24 is conveniently positive but lower than the voltage supplied to the electrode and gas supply component 36.

If the first electrode 24 is located above the electrode and gas supply component 36 and if the system performs discharging of a positive charge then the first electrode 24 can be provided with a negative voltage that can range between zero and few hundred volts. The electrode and gas supply component 36 can be provided by a negative voltage that is smaller (less negative) than the negative voltage provided to the first electrode 24.

If the first electrode 24 is located below the electrode and gas supply component 36 and if the system performs discharging of a positive charge the then the voltage supplied to the first electrode 24 is conveniently negative but larger (more negative) than the voltage supplied to the electrode and gas supply component 36.

Figure 2:
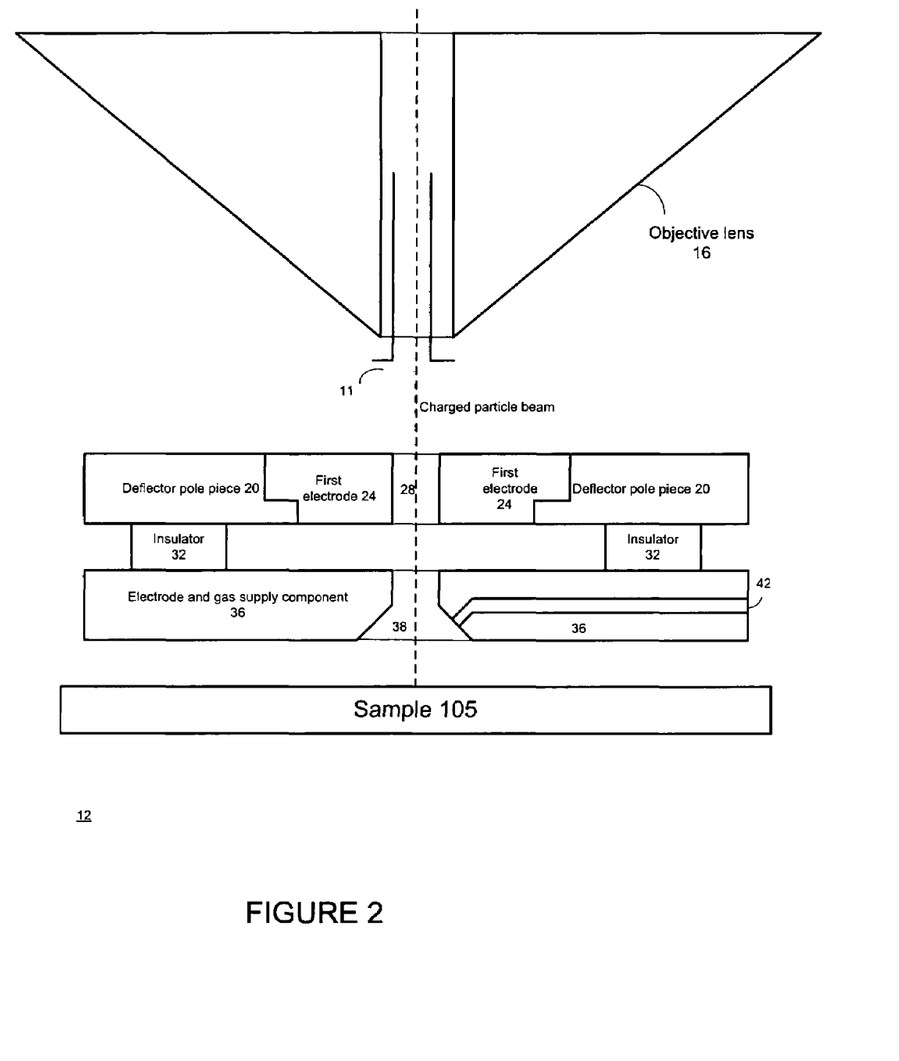
FIGS. 2–7 illustrates various electrode arrangements according to various embodiments of the invention.

Referring to FIG. 2, arrangement 12 includes first electrode 24 and electrode and gas supply component 36. The objective lens 16 is positioned above first electrode 24 that in turn is positioned above an electrode and gas supply component 36. The latter is positioned close to the sample 105.

In a deceleration area defined by electrode 11 and the subsequent electrode arrangement 24/36 the kinetic energy of electrons is usually reduced that are previously accelerated by anode 104.

The first electrode 24 can be set to a first voltage while the electrode and gas supply component 36 can be set to a second voltage. The first voltage can differ from the second voltage or can equal it. The first and voltages can be set independently from each other. By controlling the first and second voltages the system 100 can reduce positive charging of a scanned area of the sample.

The first electrode 24 is formed with a beam opening 28 for allowing a charged particle beam (either primary or secondary) to pass therethrough. The first electrode is connected to one or more deflector pole pieces 20 that in turn are connected to the upper ends of one or more insulators 32. The lower end of the at least one or more insulators 32 is connected to an upper surface of the electrode and gas supply component 36.

The electrode and gas supply component 36 is formed with an opening 38 that allows a charged particle beam to pass therethrough and also allows gas that passes through passageway 42, to be injected into the vicinity of the sample 105. The lower part of the opening is conical, but this is not necessarily so.

According to other embodiments of the invention the gas can be provided in other means, such as but not limited to, a nozzle or a conduit that is not formed within the electrode.

According to an embodiment of the invention a discharging of a negatively charged sample can include: (i) setting the combined electrode and gas supply component 36 to a second voltage that is either zero or slightly positive and (ii) injecting gas by component 36 such as to direct ions to the vicinity of the negative charge, such as to discharge the negative charge. After stages (i) and (ii) are applied the second voltage is set to a level that improves and even optimized the propagation of secondary electrons towards in-lens detector 17.

According to an embodiment of the invention a discharging of a positively charged sample can include: (i) setting the combined electrode and gas supply component 36 to a second voltage that is either zero or slightly negative and (ii) setting the first electrode 24 to a voltage level that improves and even optimized the propagation of secondary electrons towards in-lens detector 17 and that also maintains a minimal electrostatic field gradient near wafer 105.

Figure 3:
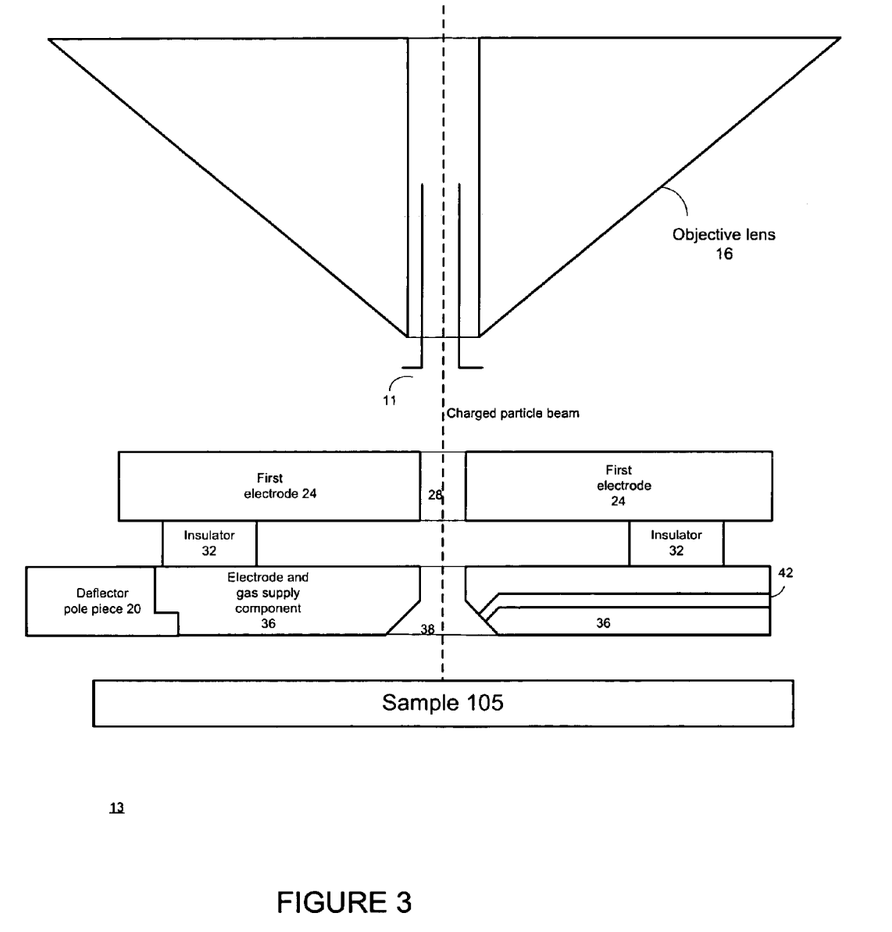

FIG. 3 illustrates an arrangement 13 that differs from arrangement 12 by having one or more deflector pole piece 20 that are connected to the electrode and gas supply component 36 instead to the first electrode 24.

Figure 4:
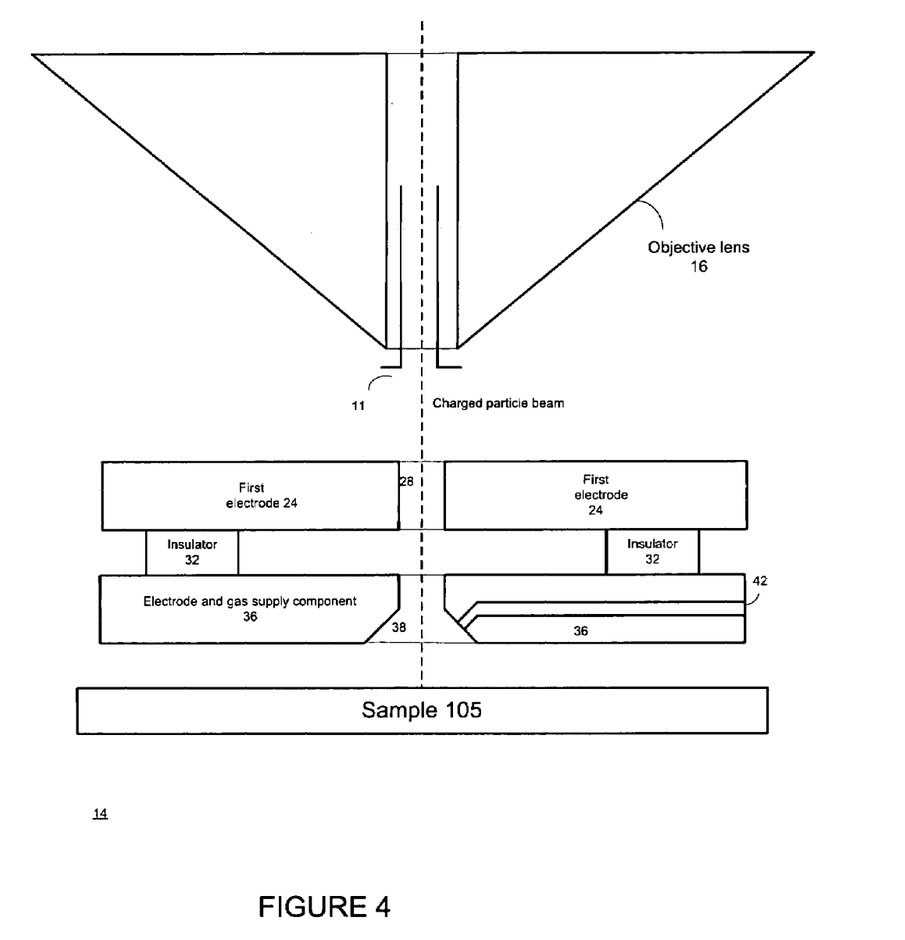

FIG. 4 illustrates an arrangement 14 that differs from arrangement 12 by not having one or more deflector pole piece 20.

Figure 5:
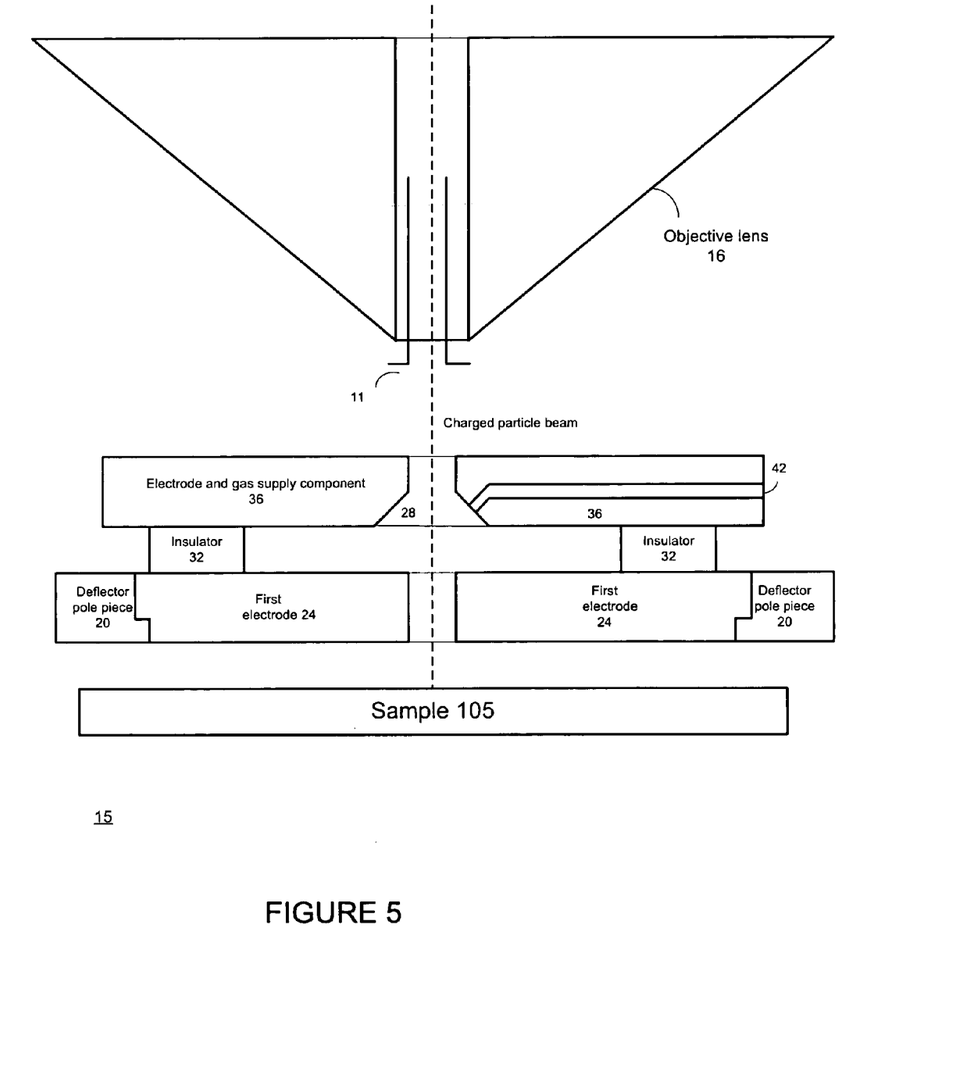

FIG. 5 illustrates an arrangement 15 in which the electrode and gas supply component 36 is positioned above one or more insulators 32. The lower end of insulators 32 are connected to an upper surface of fist electrode 24 that is turn is connected to one or more deflector pole pieces 20.

Figure 6:
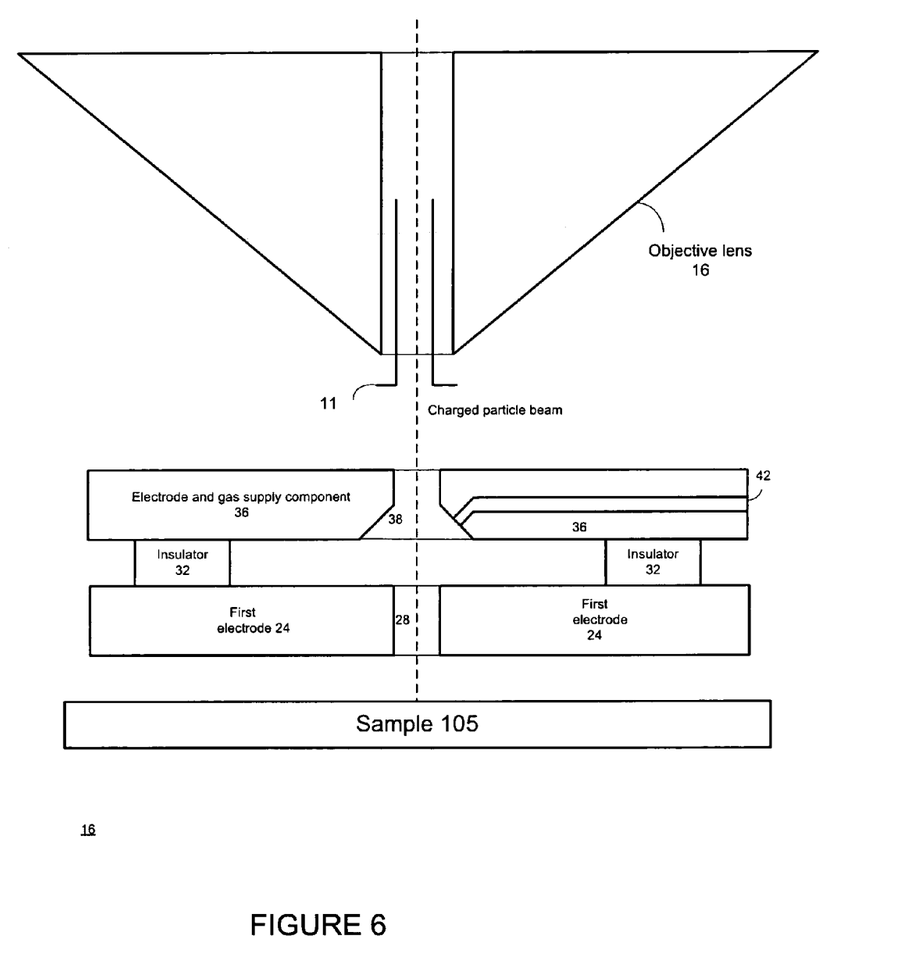

FIG. 6 illustrates an arrangement 16 that differs from arrangement 15 by not having one or more deflector pole piece 20.

Figure 7:
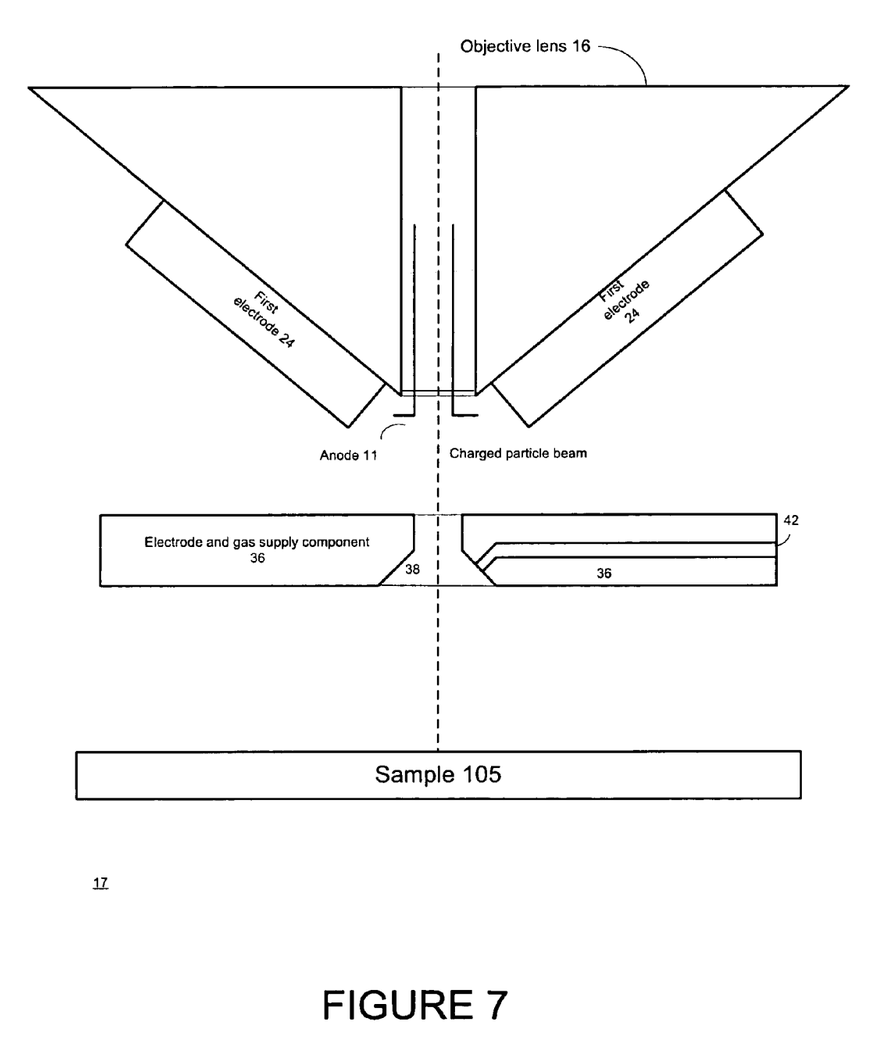

FIG. 7 illustrates an arrangement 17 in which the first electrode 24 is not parallel to the electrode and gas supply component 36.

The first electrode 24 is integrated with the objective lens 10 and is positioned above the electrode and gas supply component 36. The electrode and gas supply component 36 receives gas from nozzle 39 and is connected to deflector pole piece 20.

Figure 8:
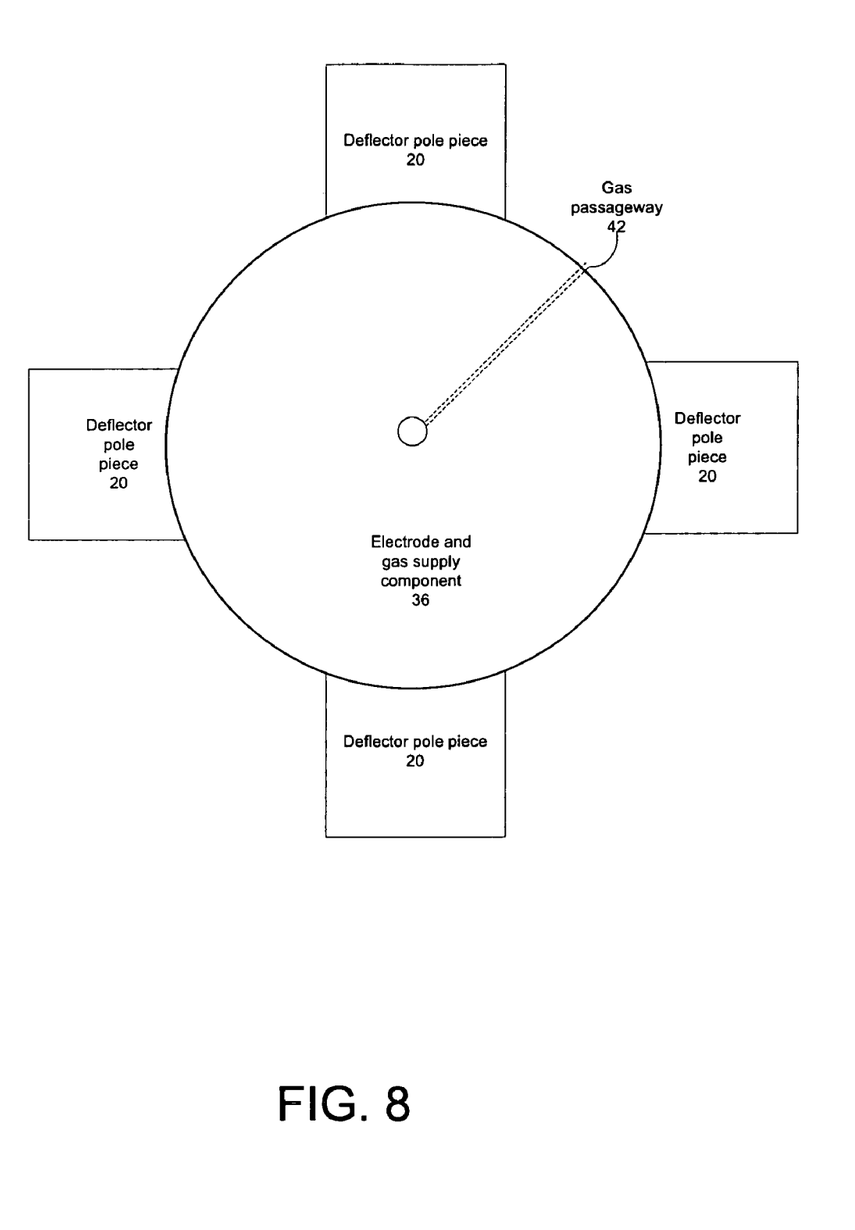
FIG. 8 illustrates multiple deflector pole pieces and an electrode and gas supply component, according to an embodiment of the invention.

FIG. 8 illustrates multiple deflector pole pieces 20 and an electrode and gas supply component 36, according to an embodiment of the invention.

The electrode and gas supply component 36 has an annular shape. Four deflector pole pieces that are arranged in a manner that each deflector pole piece is perpendicular to the adjacent deflector pole piece, are connected to the perimeter of the electrode and gas supply component 36.

FIGS. 9a–9d illustrates multiple first electrode 24 configurations, according to various embodiments of the invention.

Figure 9A:
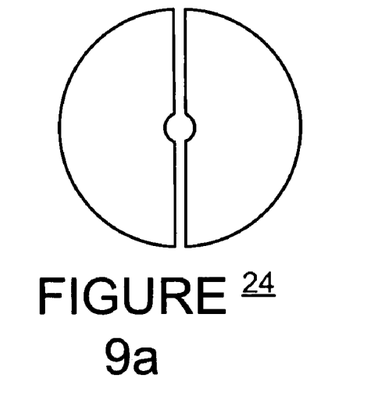
FIGS. 9a–9d illustrates multiple first electrode configurations, according to various embodiments of the invention.
Figure 9B:
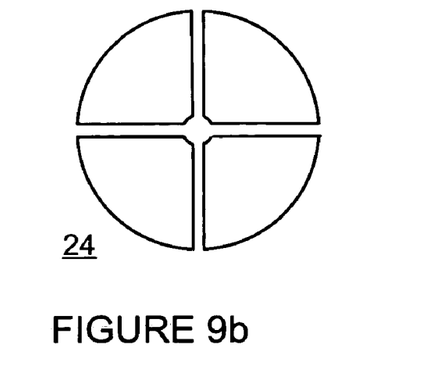
Figure 9C:
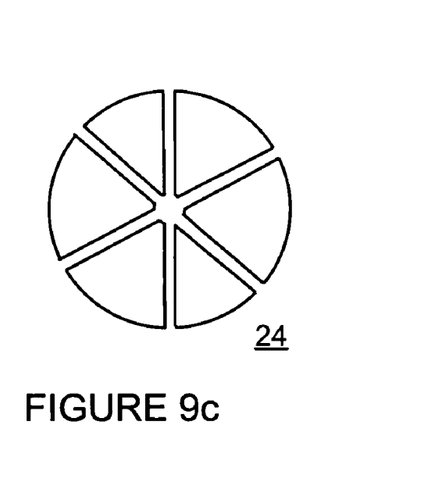
Figure 9D:
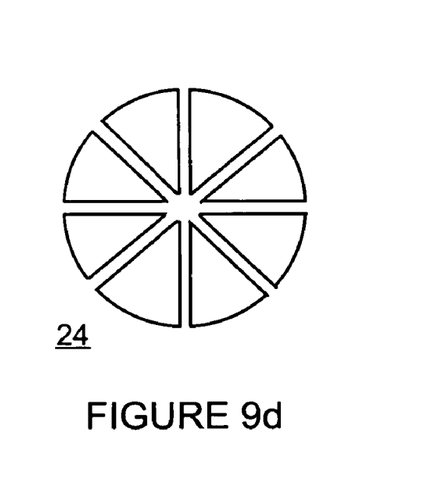

The first electrode can include multiple spaced apart portions. FIG. 9a illustrates a dual portion first electrode 24, FIG. 9b illustrates a four-part first electrode 24, FIG. 9c illustrates a six-part first electrode and, FIG. 9d illustrates an eight part first electrode 24. It is noted that all parts of a certain configuration are equal to each other but this is not necessarily so. It is further noted that first electrode 24 can have other shapes that annular shape. It is noted that each portion can receive a different supply voltage. These different voltages can be superimposed on a basic electrode voltage, for example in order to generate dipole fields for beam deflection, quardapole fields for beam stigmation and other fields for beam correction.

Figure 10:
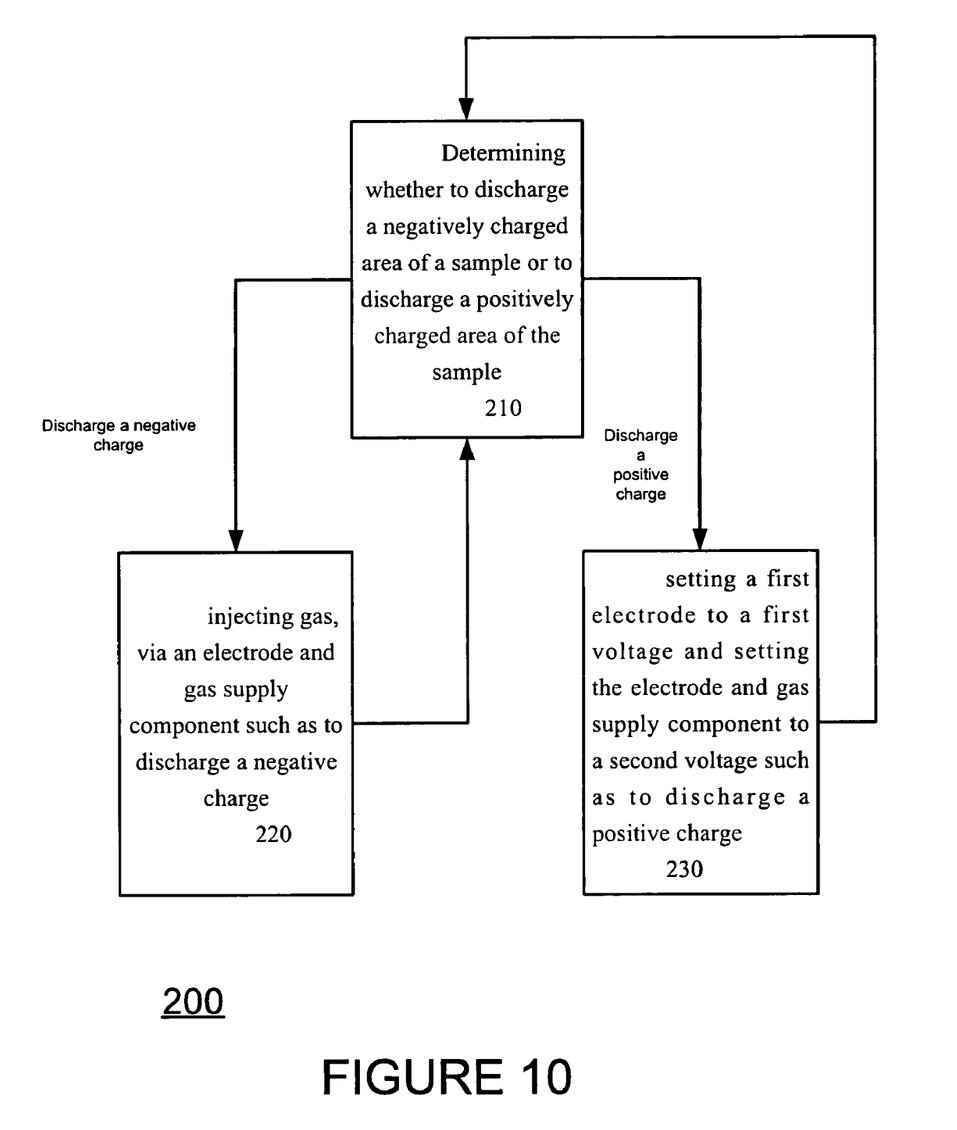
FIG. 10 is a flow chart of a method for discharging a sample, according to an embodiment of the invention.

FIG. 10 is a flow chart of a method 200 for discharging a sample, according to an embodiment of the invention.

Method 200 starts by stage 210 of determining whether to discharge a negatively charged area of a sample or to discharge a positively charged area of the sample. The determination can be based upon the images or detection signals acquired from previous or currently acquired measurement sessions, from expected charging effects, from the material and shape of the scanned sample, and the like.

If there is a need to discharge a negative charged area then stage 210 is followed by stage 220 of injecting gas, via an electrode and gas supply component, such as to discharge a negative charge.

Conveniently, stage 220 includes supplying gas through a gas passageway formed within the electrode and gas supply component. It is noted that other manners for providing gas can be applied, including providing gas through a nozzle or conduit not formed within the electrode.

If there is a need to discharge a positive charged area then stage 210 is followed by stage 230 of setting a first electrode to a first voltage and setting the electrode and gas supply component to a second voltage such as to discharge a positive charge.

According to an embodiment of the invention a combination of stages 220 and 230 can be applied to discharge negative or positively charges areas. Thus, stage 220 can be followed by (or preceded by) stage 230 when a discharge operation is required.

According to other embodiments of the invention only one of stages 220 and 230 is applied. In such embodiments, and as illustrated by FIG. 11, stages 220 and 230 are followed by stage 210. Optionally they can be followed by a control stage (not shown) that determined when to stop the pre-charging. They can stop when a certain charging is achieved, when a certain period lapses, and the like.

The method can apply in response to certain events (for example scanning an area, reception of erroneous images due to charging effects), periodically, and the like.

Conveniently, the method is practiced with one of the previously described arrangements.

Those skilled in the art will readily appreciate that various modifications and changes can be applied to the embodiments of the invention as hereinbefore described without departing from its scope as defined in and by the appended claims.

The invention claimed is:

1. A system comprising: a first electrode adapted to be set to at least a first potential; an electrode and gas supply component, adapted to be set to at least a second potential and to selectively supply gas to a vicinity of a sample; wherein the first electrode and the electrode and gas supply component are positioned close to the sample.

2. The system according to claim 1 further adapted to set at least one out of the first and second potential and determine a gas provision in response to charging of at least one area of the sample.

3. The system according to claim 1 wherein at least one out of the first electrode and the electrode and gas supply component are positioned between an objective lens and the sample.

4. The system according to claim 1 wherein at least one out of the first electrode and the electrode and gas supply component are integrated with an objective lens and the sample.

5. The system according to claim 1 wherein the first electrode is placed between the electrode and gas supply component and the sample.

6. The system according to claim 1 wherein the electrode and gas supply component is placed between the first electrode and the sample.

7. The system according to claim 1 wherein at least one insulator is connected between the first electrode and the electrode and gas supply component.

8. The system according to claim 1 wherein each of the first electrode and the electrode and gas supply component define an inner space through which charged particles can pass.

9. The system according to claim 1 wherein at least one out of the first electrode and the electrode and gas supply component are connected to at least one deflector pole-piece.

10. The system according to claim 1 wherein the electrode and gas supply component comprises an electrode formed with a gas passageway for allowing gas to pass through the electrode.

11. The system according to claim 1 wherein the electrode and gas supply comprises multiple separate electrode portions.

12. The system according to claim 1 wherein the first electrode comprises multiple separate electrode portions.

13. A method for discharging a sample, the method comprising:

determining whether to discharge a negatively charged area of a sample or to discharge a positively charged area of the sample; and injecting gas, via an electrode and gas supply component, or setting a first electrode to a first voltage and setting the electrode and gas supply component to a second voltage, in response to the determination.

14. The method according to claim 13 wherein the injecting is executed when the area is negatively charged.

15. The method according to claim 13 wherein the setting is executed when the area is positively charged.

16. The method according to claim 13 wherein at least one out of the first electrode and the electrode and gas supply component is positioned between an objective lens and the sample.

17. The method according to claim 13 wherein at least one out of the first electrode and the electrode and gas supply component is positioned between an objective lens and the sample.

18. The method according to claim 13 wherein the injecting comprises supplying gas through a gas passageway formed within the electrode and gas supply component.

19. The method according to claim 13 further comprising charging the area by a charged particle beam that passes through inner spaced defined by the first electrode and the electrode and gas supply component.

* * * * *